(12) United States Patent
Konrad et al.

(10) Patent No.: US 8,472,630 B2
(45) Date of Patent: Jun. 25, 2013

(54) METHOD AND SYSTEM FOR ESTABLISHING CRYPTOGRAPHIC COMMUNICATIONS BETWEEN A REMOTE DEVICE AND A MEDICAL DEVICE

(75) Inventors: Guido Konrad, Bern (CH); Martin Troesch, Langenthal (CH); Felix Lindner, Berlin (DE); Gregor Kopf, Berlin (DE)

(73) Assignee: Roche Diagnostics International AG, Rotkreuz (CH)

( * ) Notice: Subject to any disclaimer, the term of this patent is extended or adjusted under 35 U.S.C. 154(b) by 276 days.

(21) Appl. No.: 12/939,562

(22) Filed: Nov. 4, 2010

(65) Prior Publication Data
US 2011/0170692 A1 Jul. 14, 2011

(30) Foreign Application Priority Data
Nov. 6, 2009 (EP) ...................... 09013940

(51) Int. Cl.
*H04L 29/06* (2006.01)
(52) U.S. Cl.
USPC .......................................... 380/282; 600/364
(58) Field of Classification Search
USPC .......................................... 380/282; 600/634
See application file for complete search history.

(56) References Cited

U.S. PATENT DOCUMENTS

| | | | |
|---|---|---|---|
| 6,233,617 B1 | 5/2001 | Rothwein et al. | |
| 7,254,237 B1 | 8/2007 | Jacobson et al. | |
| 2002/0087884 A1 | 7/2002 | Shacham et al. | |
| 2003/0065918 A1 | 4/2003 | Willey | |
| 2003/0172278 A1* | 9/2003 | Farnham et al. | 713/176 |
| 2004/0034772 A1* | 2/2004 | Alao | 713/168 |
| 2010/0292556 A1* | 11/2010 | Golden | 600/364 |

FOREIGN PATENT DOCUMENTS

| | | |
|---|---|---|
| EP | 1 770 900 A1 | 4/2007 |
| EP | 1 973 265 A1 | 9/2008 |
| GB | 2 404 126 A | 1/2005 |
| WO | 2004/017600 A1 | 2/2004 |
| WO | 2008/154467 A1 | 12/2008 |

* cited by examiner

*Primary Examiner* — Michael S McNally
(74) *Attorney, Agent, or Firm* — Dinsmore & Shohl LLP

(57) ABSTRACT

A method and system establishing cryptographic communications between a remote device and a medical device, with the medical device having less processing power than the remote device are disclosed. The method may comprise establishing unencrypted communication between the remote device and the medical device, generating an asymmetric key pair by the remote device comprising a public key and a private key, generating a key request message and sending of the key request message together with the public key to the medical device, generating a pre-master key and encryption of the pre-master key with the received public key by the medical device, generating a key response message and sending of the key response message together with the encrypted pre-master key from the medical device to the remote device, decrypting the encrypted pre-master key with the private key by the remote device, and deriving a master key as a symmetric key from the pre-master key.

18 Claims, 4 Drawing Sheets

METHOD AND SYSTEM FOR ESTABLISHING CRYPTOGRAPHIC COMMUNICATIONS BETWEEN A REMOTE DEVICE AND A MEDICAL DEVICE

TECHNICAL FIELD

The present disclosure relates to a method and system for establishing cryptographic communications between a remote device and a medical device. Both the remote device and the medical device are electronic devices with some processing power.

BACKGROUND

A remote device may be, for example, a communication device, a blood glucose meter, a smart phone, a personal digital assistant (PDA), a personal computer (PC), or a remote terminal representing a remote infusion pump display on which data from the medical device is displayed to a user. The remote device may also include a bolus advisor by which the user can command the administration of insulin through the infusion pump and on which the delivery history of the infusion pump is displayed. For example, the remote device could be a diabetes management device with the medical device being the infusion pump. Other types of medical devices and remote devices are possible.

A conventional method for pairing and authenticating a medical device with a remote device is where Bluetooth is used for the pairing. For example, authenticating a 10 digit PIN generated by the medical device has to be entered by the user into the remote device. A PIN with more or less digits, for example, an 8 digit PIN, may be used. Then, the medical device and the remote device each generate a signature from the PIN. The remote device sends its signature to the medical device and compares the signature generated by the remote device to the signature generated by the medical device. If the signatures are the same, authentication has been successful. Manually entering a PIN is challenging and difficult for the user. Furthermore, for the PIN to be secure, it usually has to have a large number of digits, i.e. up to 40, which makes entering the PIN even more challenging and difficult for the user. Limited displays and user interfaces can also prove challenging and difficult for a large PIN.

A more secure key exchange can be obtained by public-key cryptography that uses an asymmetric-key method. With an asymmetric-key method the key used to encrypt a message is not the same as the key used to decrypt it. Each user has a pair of cryptographic keys—a public key and a private key. The private key is kept secret, while the public key may be widely distributed. Messages are encrypted with the recipient's public key and can only be decrypted with the corresponding private key. Even though the keys have a mathematical relationship, the private key usually cannot be derived from the public key. Examples for asymmetric-key methods are the Diffie-Hellman key exchange, the RSA method, the Transport Layer Security (TLS), the Rabin technique, the Elgamal cryptosystem, and cryptosystems based on elliptical curves.

While assymetric-key methods have the advantages that sender and recipient do not have to share identical keys to communicate securely and do not require a secure initial exchange of a secret key, compared to symmetric-key methods—assymetric key methods often rely on complicated mathematical computations and, hence, require more processing power than symmetric-key methods or run slower on systems with comparable processing power. Symmetrickey cryptosystems are generally much less computationally intensive and more efficient than comparable assymetric-key cryptosystems. In practice, asymmetric-key methods are typically s slower than comparable symmetric-key methods, which can be challenging and difficult for existing battery-driven devices, for example, embedded devices (such as an insulin pump), due to their limited processing power, clock rate and memory capacity. With the known asymmetric-key methods, for example, the RSA method, the encryption is significantly faster than the decryption, i.e. more processing power is required for decryption.

SUMMARY

In one embodiment, a method for establishing cryptographic communications between a remote device and a medical device having less processing power than the remote device is disclosed. The method may comprise one or more of the following processes, which comprises: establishing unencrypted communication between the remote device and the medical device; generating an asymmetric key pair by the remote device, the asymmetric key pair comprising a public key and a private key; generating a key request message by the remote device and sending of the key request message together with the public key to the medical device; generating a pre-master key by the medical device and encryption of the pre-master key with the received public key by the medical device; generating a key response message by the medical device and sending of the key response message together with the encrypted pre-master key from the medical device to the remote device; decrypting the encrypted pre-master key with the private key by the remote device; and deriving a master key as symmetric key from the pre-master key by either using the pre-master key as master key or by using the key request message or the key response message for the derivation of the master key from the pre-master key by each of the medical device and the remote device, the master key to be used for both decryption and encryption of application data to be communicated, wherein the key request message and/or the key response message contain random data and a time stamp.

In another embodiment, there is disclosed a system for establishing cryptographic communications, the system comprises a remote device and a medical device which performs the methods disclosed and described herein.

DETAILED DESCRIPTION OF DRAWINGS

Additional embodiments are included in the following description of the drawings illustrating the present disclosure. In the drawings like reference numerals designate the same or similar parts or method acts throughout the several figures of which:

DETAILED DESCRIPTION

Figure 1:
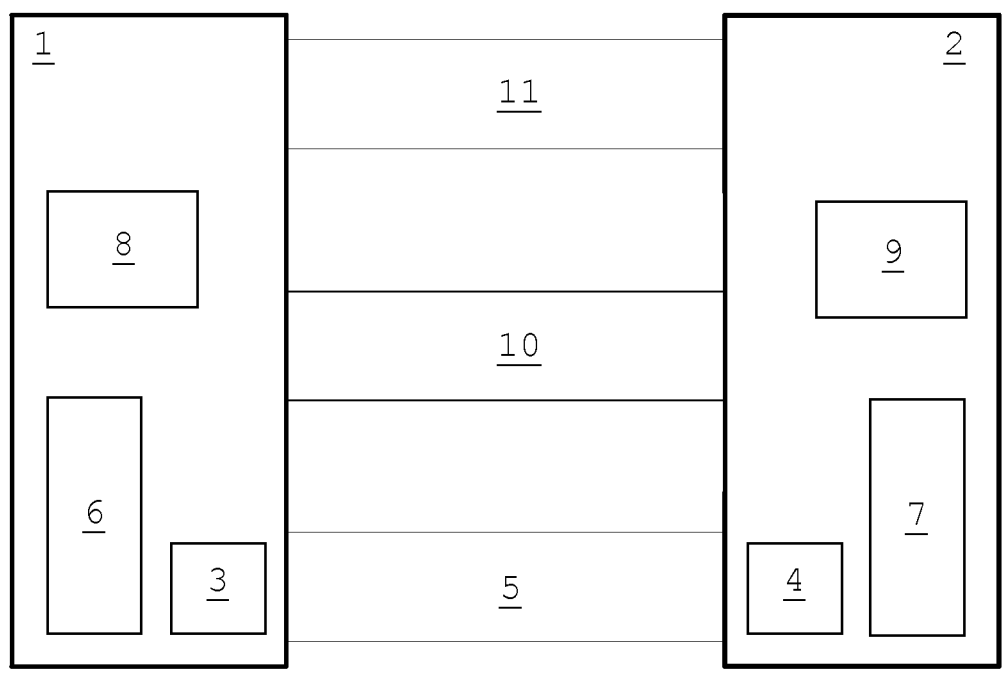
FIG. 1 shows an abstract interconnection layer model for wireless communications between a medical device and a remote device.

A method and system for establishing cryptographic communications between a remote device and a medical device, the medical device having less processing power than the remote device, by which secured communications between a medical device and a remote device can be ensured are disclosed. A secured communication protects the communicated data against unauthorized access, use, disclosure, disruption, modification, destruction and so forth. The present disclosure provides further a method for establishing cryptographic communications between a remote device and a medical device, the medical device having less processing power than the remote device, by which secured communications between a medical device and a remote device can be established and whose security corresponds to the security that can be achieved with assymetric-key algorithms while requiring less processing power.

In other embodiments, a method and system for establishing cryptographic communications between a remote device and a medical device, for example, an insulin pump, the medical device having less processing power than the remote device, are disclosed. The method may comprise establishing unencrypted communication between the remote device and the medical device, generating an asymmetric key pair by the remote device, the asymmetric key pair comprising a public key and a private key, generating a (e.g., client) key request message by the remote device and sending the key request message together with the public key to the medical device, generating a pre-master key by the medical device and encrypting the pre-master key with the received public key by the medical device, generating a (e.g., server) key response message by the medical device and sending of the key response message together with the encrypted pre-master key from the medical device to the remote device, decrypting the encrypted pre-master key with the private key by the remote device, and deriving a master key as symmetric key from the pre-master key by either using the pre-master key as master key (i.e. the master key corresponds to or is identical with the pre-master key) or by using the key request message or the key response message by each of the medical device and the remote device for the derivation of the master key from the pre-master key, the master key to be used for decryption and encryption of application data to be communicated between the medical device and the remote device. Besides decryption and encryption the master key may optionally also be used for authentication purposes.

Regarding the first established unencrypted communication between the remote device and the medical device, it is noted that for this so-called unencrypted communication a communication protocol may be used for the communication between the medical device and the remote device that may comprise its own additional and self-contained encryption, for example, Bluetooth present disclosure The generated master key can be used to encrypt and decrypt application data to be communicated according to a symmetric cryptography method based on, for example, AES (Advanced Encryption Standard), DES (Data Encryption Standard), IDEA (International Data Encryption Algorithm), Blowfish, Twofish or the like.

The method may employ the RSA method, such that the asymmetric key pair generated by the remote device is an RSA key pair, or another asymmetric-key communications method where encryption is faster than decryption for generation of the asymmetric key pair and for encryption and decryption of the pre-master key.

The remote device acts as client, while the medical device acts as server. A so-called key request message is defined as a message sent to announce the presence of a device, i.e. with the key request message the remote device announces its presence to the medical device, and with the key response message the medical device announces its presence to the remote device.

The method is unsymmetrical in that encryption of the pre-master key, which requires significantly less processing power than its decryption, takes place on another device, namely the medical device, than the decryption which takes place on the remote device. Hence, the method may be used for set-ups of two devices, wherein one of the devices has low processing power and/or low memory. The computationally expensive decryption is left to the computationally stronger device and the medical device with limited processing power only performs the encryption. Furthermore, the method makes manually entering a PIN redundant.

In one embodiment, the method combines public-key cryptography (using an asymmetric key pair) with the efficiency of symmetric-key cryptography (with the master key) and thus constitutes a so-called hybrid cryptosystem. In other embodiments, the method may use public-key cryptography until the pre-master key, which has been encrypted with the public key by the medical device, has been sent to and decrypted by the remote device with the private key to ensure secure communication of the pre-master key. A master key, as the symmetric key, is derived from the pre-master key to increase security. The master key is then used within a more efficient symmetric-key cryptosystem for encryption and decryption and/or authentication of the application data that shall be communicated between the remote device and the medical device.

The term "encryption" may be understood as the process of transforming data/information to make it unreadable to anyone except those possessing special knowledge, i.e. the key, for decrypting the data/information, thereby reversing the process of encryption to make the data/information readable again. The term "authenticating" may be understood as the process of verifying the identity of a device (or a person or an application, respectively).

The method may further comprise a verification act, the verification act comprising the remote device and the medical device each computing verification data, wherein the master key and, in one aspect, the previously exchanged client and key response messages are used for the computation of verification data. The remote device and the medical device each display the verification data to the user, who is prompted to confirm that the verification data computed by the remote device and the verification data computed by the medical device have the same values. After the user has confirmed that the verification data computed by the remote device and the verification data computed by the medical device are identical, cryptographically secured communication of application data between the remote device and the medical device may be started. Verification prevents attacks, such as man-in-the-middle attacks.

In cryptography, a man-in-the-middle attack is a form of active eavesdropping, where the attacker makes independent connections with the victims and relays messages between them, while making them think that they are talking directly to each other over a private connection when, in fact, the entire conversation is controlled by the attacker. For a successful man-in-the-middle attack, the attacker must be able to intercept all messages going between the two victims and to inject new messages, i.e. the attacker has to be able to impersonate each communication endpoint to the satisfaction of the other. Through verification, it can advantageously be ensured that messages sent from the remote device to the medical device and vice versa (such as the key request message together with the public key, or the key response message together with the encrypted pre-master key) have not been manipulated by an attacker.

The present disclosure provides further a system comprising of a remote device and a medical device, for example, an insulin pump, with the medical device having less processing power than the remote device, wherein the system is designed to carry out the method of the present disclosure. Reference is now made to the figures, in which various exemplary embodiments are depicted and described hereinafter.

FIG. 1 shows a medical device 1 and a remote device 2 along with an abstract interconnection layer model for wireless communication between the two devices 1 and 2. The medical device 1 may be a mobile medical device such as an insulin pump. The remote device 2 may be, for example, a glucose meter or a personal computer. The medical device 1 includes a wireless communication module 3 and the remote device 2 also includes a wireless communication module 4. The wireless communication modules 3 and 4 communicate with each other wirelessly via a communications layer 5. The wireless communication modules 3 and 4 each include a dedicated processor connected to a wireless transmitter and a wireless receiver, or to a wireless transceiver. The wireless communication modules 3 and 4 are configured to communicate with each other using any conventional wireless medium including, for example, radio frequency (RF), infrared (IR), microwave, inductive coupling, or the like. The communications layer 5 supports the chosen wireless medium. The communication modules 3 and 4 may, for example, each be configured to communicate via RF according to a conventional BlueTooth® radio frequency communications protocol, and the communications layer 5 may accordingly be a conventional BlueTooth® communications layer.

The medical device 1 and the remote device 2 each further include a control unit 6 and 7 respectively. The control units 6 and 7 may be or include a microprocessor, although either or both of the control units 6 and 7 may additionally or alternatively include other control circuits. The medical device 1 and the remote device 2 each further include a user interface 8 and 9, respectively. The user interfaces 8 and 9 may be visual display units, each of which may be or include a conventional liquid crystal display (LCD), one or more light emitting diodes (LEDs), a vacuum fluorescent display or the like. The user interfaces 8 and 9 may also comprise an audible device that is responsive to a control signal to produce an audible sound and a tactile device configured to be responsive to a control signal to produce a tactile signal that may be perceived by a user. The user interfaces 8 and 9 may also comprise a unit that receives/provides, such as keys, a touch screen, or the like.

After unsecured communication between the medical device 1 and the remote device 2 via the communications layer 5 has been established, the medical device 1 and the remote device 2 are wirelessly connected by a security and transport layer 10. Physically, the security and transport layer 10 may form a single layer as shown in FIG. 1, or it may instead be partitioned into a security layer and a separate transport layer. In either case, the asymmetric-key cryptographic part of the method of the present disclosure and the derivation of the symmetric key take place via the security portion of the security and transport layer 10, for example, the generation of an asymmetric key pair, generation of a key request message and sending of the key request message together with the public key to the medical device, generation and encryption of a pre-master key by the medical device, generation of a key response message and sending of the key response message together with the encrypted pre-master key to the remote device, decryption of the encrypted pre-master key with the private key by the remote device, derivation of a master key, and the optional verification step are performed on the security and transport layer(s) 10 of the medical device 1 and of the remote device 2. Following successful generation of the master key, a secure link (i.e. secure communications) is established between the medical device 1 and the remote device 2, and application data can be transmitted between the two devices 1 and 2 via an application layer 11. When the medical device 1 and the remote device 2 communicate wirelessly in a secure manner, the transport portion of the security and transport layer 10 may be optionally used for error recognition and retransmission of data.

Figure 2:
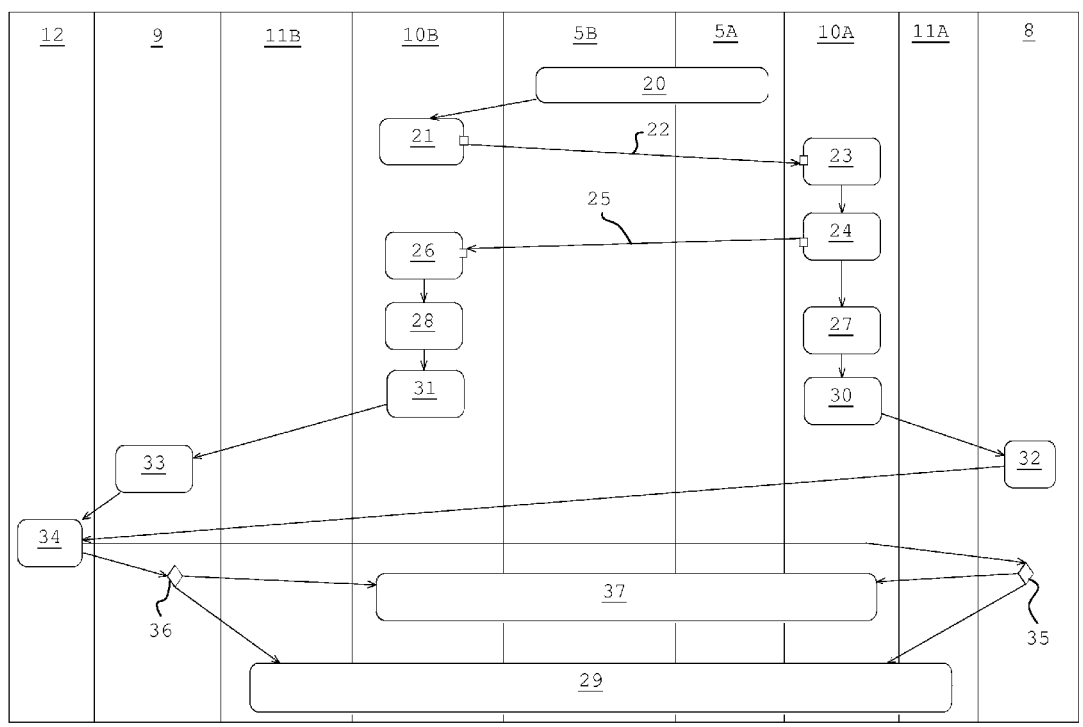
FIG. 2 shows a flowchart of an embodiment.

Referring to FIG. 2, a flowchart is shown of a first embodiment of the method according to the present disclosure. The columns of FIG. 2 indicate the entities to which a certain method step or action is allocated. Column 5A represents the communications layer of the medical device 1. Column 5B represents the communications layer of the remote device 2. Column 10A represents the security and transport layer of the medical device 1. Column 10B represents the security and transport layer of the remote device 2. Column 11A represents the application layer of the medical device 1. Column 11B represents the application layer of the remote device 2. Column 8 represents the user interface of the medical device 1. Column 9 represents the user interface of the remote device 2. Column 12 represents the user who is expected to perform an action.

In process 20, communication between the medical device 1 and the remote device 2 is established via the communications layers 5A, 5B, the communication being neither authenticated nor encrypted. The amount of communication connections that the medical device 1 can accept in a certain time frame may be limited to prevent denial-of-service attacks and to prevent an attacker from gaining too much insight into the cryptographic actions performed by the medical device 1.

In process 21 the remote device 2 generates, in its security and transport layer 10B, an asymmetric RSA key pair that comprises an RSA public key and an RSA private key, each RSA key may contain at least 2048 bits. In process 22, the remote device 2 then generates a key request message and sends it via the security and transport layers 10B, 10A to the medical device 1, thereby indicating that the remote device wishes to start the key exchange protocol. Along with the key request message, the remote device 2 sends the RSA public key to the medical device, which the medical device 1 shall use for encryption. For sending, the RSA public key is preferentially PEM encoded (PEM=Privacy-enhanced Electronic Mail). The key request message may contain random data, for example, 28 random bytes, and a time stamp, for example, a 4 byte time stamp, to prevent replay attacks. For generation of the random bytes, e.g. the Blum-Blum-Shub generator may be used or the less secure, but significantly faster, ISAAC random number generator (ISAAC=Indirection, Shift, Accumulate, Add, and Count). The length of the public key that the medical device 1 has to accept can be restricted to avoid using computationally expensive keys.

In process 23, the medical device 1 generates a pre-master key and encrypts the pre-master key in process 24 by the RSA public key that it has received from the remote device 2. For generation of the pre-master key, the medical device 1 may choose a random 32 byte key in its security and transport layer 10A. In process 25, the medical device 1 generates a key response message and answers the key request message by sending the key response message along with the encrypted pre-master key via the security and transport layers 10A, 10B to the remote device 2. For sending, the encrypted pre-master key is preferentially OAEP padded (OAEP=Optimal Asymmetric Encryption Padding) or padded in accordance with another secure padding function. The key response message may contain random data, for example, 28 random bytes, and a time stamp, for example, a 4 byte time stamp, to prevent replay attacks. For generation of the random bytes, the so-called Blum-Blum-Shub generator or the so-called ISAAC random number generator may be used.

In process 26, the remote device 2 decrypts the received encrypted pre-master key using its RSA private key in its security and transport layer 10B. In processes 27 and 28, both the medical device 1 and the remote device 2 use the random values exchanged in the key request message and the key response message to derive a new key, namely the master key, from the pre-master key in the security and transport layers 10A, 10B. The master key is preferentially derived from the pre-master key by means of a pseudo-random function (PRF) whose parameters are—apart from the pre-master key—in particular the random bytes contained in the key request message and in the key response message and may include an additional fixed string such as, for example, the string "master secret." The pseudo-random function may make use of one or two or more different hash functions such as, for example, MD5 (Message-Digest Algorithm 5), SHA™ (SHA=Secure Hash Algorithm), RIPEMD-160 (RIPEMD=RACE Integrity Primitives Evaluation Message Digest), SHA-224, and SHA-256, with RIPEMD-160 and SHA-224 or RIPEMD-160 and SHA-256 being combinations of two hash functions. The generated master key can then be used in process 29 as symmetric key within a symmetric-key cryptosystem to authenticate and encrypt application data that shall be communicated and exchanged between the medical device 1 and the remote device 2 on the application layers 11A, 11B.

To avoid attacks, such as man in the middle, the method comprises a verification act before the application data that is encrypted with the master key is actually transmitted via the application layers 11A, 11B in process 29, to ensure that the messages exchanged in processes 22 and 25 between the medical device 1 and the remote device 2 (also called protocol messages) have not been manipulated by an attacker.

In processes 30 and 31, both the medical device 1 and the remote device 2 compute, independently from one another, verification data (also called authentication data) in the security and transport layers 10A, 10B as parameters, in one aspect, by using a pseudo-random function with the previously derived master key and the previously exchanged protocol messages, i.e. with the master key, the key request message along with the public key and the key response message along with the encrypted pre-master key as parameters. In one embodiment, the verification data may each consist exemplarily of 12 bytes, but may consist of more or less bytes, e.g. of 8 bytes, for practical purposes in still other embodiments. In processes 32 and 33, both the medical device 1 and the remote device 2 display the verification data they each computed on their respective user interfaces 8, 9 to the user 12. In process 34, the user 12 has to compare the verification data displayed on the user interface 8 of the medical device 1 with the verification data displayed on the user interface 9 of the remote device 2. Then, in processes 35, 36, the user 12 has to receive/provide information to both user interfaces 8, 9. If the user confirms in processes 35, 36 by an appropriate user input (receiving/providing) that the displayed verification data are actually identical (i.e. if authentication is confirmed), then the method may proceed to process 29 and the cryptographically secure exchange/communication of application data via application layers 11A, 11B may be started. If, however, in processes 35, 36, the user 12 does not confirm that the displayed verification data are identical (i.e. if authentication is not confirmed) or if the verification step is cancelled, then the connection establishing on the security and trans-port layers 10A, 10B is terminated and communication between the medical device 1 and the remote device 2 on the communications layers 5A, 5B is abandoned in process 37.

If the medical device 1 and the remote device 2 already exchanged cryptographic key information in the form of the public key and the pre-master key and if both have computed the master key, then the devices 1 and 2 may re-use the already computed master key in one or more subsequent sessions, thereby resuming the previous session, without the need to first compute a new asymmetric key pair, exchange a public key and compute and exchange a new pre-master key, i.e. without the need for negotiating new keys. To provide the option of session resumption, the key request message and preferably also the key response message each comprise a session identifier that may be, e.g., 32 bits, but can also contain more or less bits depending on boundary conditions, safety requirements, and other parameters.

If the remote device 2 wants to end a currently running session where the master key has already been computed and application data may already have been exchanged in process 29, then the remote device sends a key request message containing null-bits as session identifier to the medical device 1 to indicate that the remote device 2 does not wish to continue the current session (not shown). Upon receipt of this key request message, the medical device 1 chooses a random unique session identifier for the current session and sends it within the key response message to the remote device 2 (not shown). Both the remote device 2 and the medical device 1 then store the session identifier chosen by the medical device 1, along with the master key derived in the current session, in their respective memory or electronic storage repository, provided that generation of the master key and key exchange is complete (not shown). With the session identifier and the corresponding master key being stored in the respective storage repository of the remote device 2 and the medical device 1, the previous session can be resumed later without the need of re-negotiating a new master key.

Figure 3:
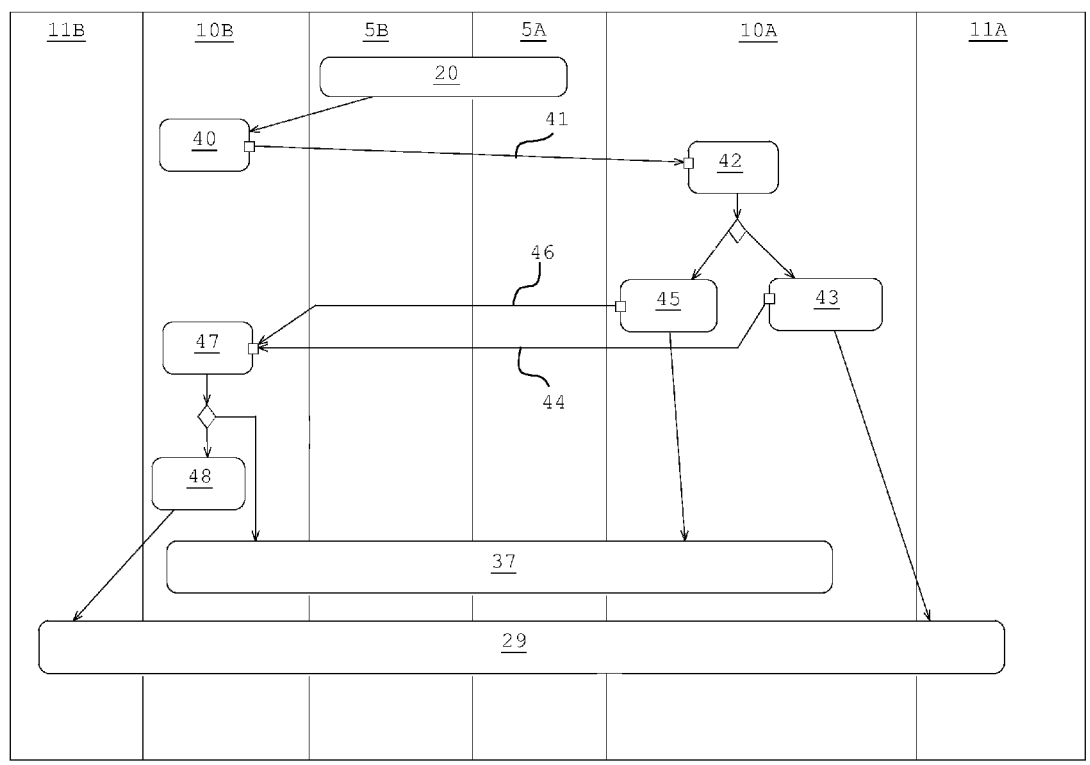
FIG. 3 shows a flowchart of a resumption of a session which has been started in accordance with the embodiment shown in FIG. 2.

FIG. 3 depicts a flowchart of a resumption of a previous session, the previous session having been started as shown in FIG. 2. The verification act depicted in FIG. 2 (i.e. processes 30 to 36) is not shown but may also form part of the embodiment of the present disclosure to prevent an attack, such as, e.g., a man-in-the-middle-attack. The additional numbers that remain the same as the numbering in FIG. 1 also have the same meaning.

As with the embodiment in FIG. 2, in process 20 unencrypted and unauthenticated communication is established between the medical device 1 and the remote device 2 via the communications layers 5A, 5B. If the remote device 2 wishes to resume a previous session whose session identifier and master key have been stored, it requests resuming of the previous session by generating a key request message that contains the session identifier of the session to be resumed (process 40) and sends it via the security and transport layers 10B, 10A to the medical device 1 (process 41). Upon receipt of the key request message, the medical device decides in process 42 whether to accept the request for session resumption or whether to decline the request. For example, for each session there may be assigned a certain validity time after which the session is considered invalid and may not be resumed and after which a request to resume this session is declined by the medical device 1, so that a new session has to be started and established.

If the medical device 1 accepts the request for session resumption in process 43, because the validity time of the previous session to be resumed has not expired, it generates a key response message containing the session identifier of the session to be resumed, reads the master key of the session to be resumed from its storage repository and sends the key response message in process 44 to the remote device 2. If the medical device 1, however, declines the request for session resumption in process 45, for example because the session's validity time has expired, then it generates a key response message containing only null-bits as session identifier, sends this key response message in 46 to the remote device 2, stops the connection establishing on its security and transport layer 10A and disconnects/closes the connection between the medical device 1 and the remote device 2 on its communications layer 5B in process 37.

Upon receipt of the key response message the remote device 2 checks in process 47 the validity of the session identifier that the key response message contains. If this session identifier is invalid, i.e. contains only null-bits, the remote device 2 moves to process 37 and stops the connection establishing on its security and transport layers 10B and disconnects/closes the connection between the medical device 1 and the remote device 2 on its communications layer 5B. The remote device 2 then has to start a new session with the medical device 1 as described in FIG. 1 to negotiate keys and to derive a new master key. If the session identifier of the key response message, however, corresponds to the session of which resumption has been requested, then the remote device 2 reads in process 48 the stored master key from its storage repository and communication and exchange of application data that is authenticated and encrypted with the master key is resumed with the medical device 1 in process 29.

Figure 4:
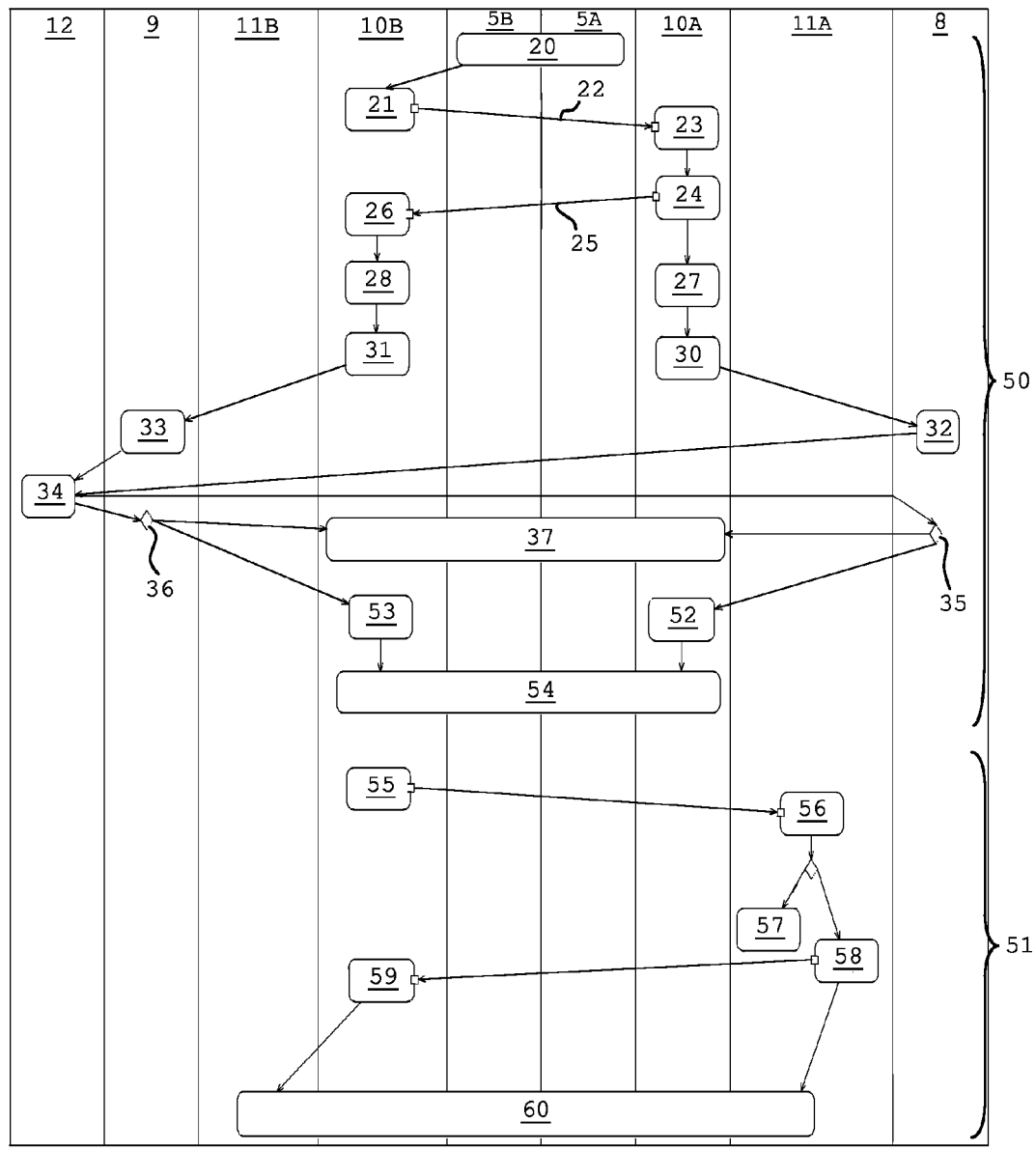
FIG. 4 shows a flowchart of another embodiment.

According to another embodiment, the connection between the medical device 1 and the remote device 2 may be closed and communication between the two devices 1 and 2 is thus terminated after the derivation of the master key or, if applicable, after the performing of the verification act, i.e. after the user has confirmed that the verification data computed by the remote device 2 and by the medical device 1 have the same values, i.e. the connection between the medical device 1 and the remote device 2 is closed after the pairing of the two devices 1 and 2 is complete. In this embodiment, communication/connection between the medical device 1 and the remote device 2 has to be established anew after the closing of the connection after successful pairing, so that key exchange and connection establishing for application data exchange are split into two separate process parts to be performed by the remote device 2 and the medical device 1. Referring to FIG. 4, reference numeral 50 denotes a flowchart of the key exchange part and reference numeral 51 denotes a flowchart of the subsequent connection establishing part for application data exchange. The verification act depicted in FIG. 2 (i.e. processes 30 to 37) is optional and may be omitted. The additional numbers that remain the same as the numbering in FIG. 1 also have the same meaning.

The key exchange part 50 corresponds to the embodiment depicted in FIG. 2 and the above description apart from process 29 and it is herewith referred to the above description thereof. In the key exchange part 50, the combination of the key request message and the public key that is sent in process 22 from the remote device 2 to the medical device 1 may take the form of a dedicated key exchange message in form of a key request message whose parameters are the public key (for example, an RSA public key) and a session identifier, without random values. For a new session, this session identifier contains only null-bits. Similarly, the combination of the key response message and the encrypted pre-master key that is sent in process 25 from the medical device 1 to the remote device 2 takes the form of a dedicated key exchange message in form of a key response answer whose parameters are the encrypted pre-master key and the session identifier without additional random values, the session identifier being chosen by the medical device 1 to identify the current session. Regarding resumption of a previous session, combinations of the key exchange part 50 with the embodiment depicted in FIG. 3 are possible.

After the master key has been derived in processes 28 and 29, and, if a verification act is provided as depicted in FIG. 4, after the user 12 has confirmed in processes 35, 36 that the displayed verification data are identical (i.e. after authentication is confirmed), the medical device 1 and the remote device 2 store the computed master key each in their respective storage repository in processes 52 and 53 and it is established in process 54 that pairing of the medical device 1 and the remote device 2 is completed with the connection between the medical device 1 and the remote device 2 being closed on the communications layers 5A, 5B, if no further actions on levels higher than the communications layers 5A, 5B (e.g. on the security and transport layers 10A, 10B) are planned.

For re-establishing connection between the medical device 1 and the remote device 2, the remote device 2 sends, in process 55 of the connection establishing part 51 a connection request, a so-called SYN-message (synchronizing message), to the medical device 1 via the security and transport layers 10A and 10B, the connection request containing the session identifier assigned in the key exchange part 50. In process 56, the medical device 1 checks if the session identifier is valid, whether the validity time of the session that the session identifier has been assigned to has not expired. If the session identifier is invalid, the medical device 1 silently discards the connection request in process 57, which the remote device 2 then notices through timeout. If the medical device 1 deems the session identifier to be valid, it accepts the connection request and sends, in process 58, an acknowledgement message, a SYN-acknowledgement message, to the remote device 2 via the security and transport layers 10A and 10B and reads the stored master key of the identified session from its storage repository. The acknowledgement message has the session identifier as parameter. Presently, communication between the medical device 1 and the remote device 2 is neither authenticated nor encrypted. Upon receipt of the acknowledgement message, the remote device 2 reads in process 59 the stored master key of the identified session from its storage repository. Then, the remote device 2 starts in process 60 with the exchange of application data with the medical device 1 via the application layers 11A and 11B, the application data being authenticated and encrypted with the master key.

Having described the various embodiments of the present invention in detail and by reference to specific illustrated embodiments thereof, it will be apparent that modification and variations are possible without departing from the scope of the invention defined in the appended claims.

What is claimed is:

1. A method for establishing cryptographic communications between a remote device and a medical device, with the medical device having less processing power than the remote device, comprising:

establishing unencrypted communication between the remote device and the medical device;

generating an asymmetric key pair by the remote device, the asymmetric key pair comprising a public key and a private key;

generating a key request message by the remote device and sending of the key request message together with the public key to the medical device;

generating a pre-master key by the medical device and encryption of the pre-master key with the received public key by the medical device;

generating a key response message by the medical device and sending of the key response message together with the encrypted pre-master key from the medical device to the remote device;

decrypting the encrypted pre-master key with the private key by the remote device; and deriving a master key as symmetric key from the pre-master key by either using the pre-master key as master key or by using the key request message or the key response message for the derivation of the master key from the pre-master key by each of the medical device and the remote device, the master key to be used for both decryption and encryption of application data to be communicated, wherein the key request message and/or the key response message contain random data and a time stamp; and wherein the remote device and the medical device each compute verification data using the master key and each display the computed verification data to a user, and wherein communication of the application data may first start after the user has confirmed that the verification data computed by the remote device and the medical device have the same values.

2. The method of claim 1, wherein the medical device is an insulin pump.

3. The method of claim 1, wherein the asymmetric key pair is an RSA key pair.

4. The method of claim 1, wherein the time stamp is a four byte time stamp.

5. The method of claim 1, wherein the key request message and/or the key response message contain a session identifier.

6. The method of claim 5, wherein requesting resuming of a previous session the key request message that the remote device sends to the medical device contains the session identifier of the session that shall be resumed.

7. The method of claim 6, wherein receipt of a key request message with a session identifier the medical device has the option of accepting or declining the request to resume the session identified by the session identifier.

8. The method of claim 7, wherein a validity time period is defined after a request to resume a session is declined, so a new session has to be started.

9. The method of claim 7, wherein if the medical device declines a request to resume a session, the key response message that the medical device sends to the remote device contains null-bits as session identifier, and wherein after sending of the key response message the medical device terminates communication.

10. The method of claim 9, wherein the remote device terminates communications after the medical device has declined the request to resume a session.

11. The method of claim 7, wherein the medical device reads the master key of the session to be resumed from a storage repository and sends a key response message to the remote device that contains the session identifier of the session to be resumed, if the medical device accepts a request to resume a session.

12. The method of claim 11, wherein the remote device reads the master key of the session to be resumed from storage repository if the medical device accepts the request to resume a session, with the master key to be used for both decryption and encryption of the application data to be communicated.

13. The method of claim 11, wherein after the derivation of the master key or if applicable after the user has confirmed that the verification data computed by the remote device and the medical device have the same values the pairing of the medical device and the remote device is completed and communication between the medical device and the remote device is terminated.

14. The method of claim 13, wherein after termination of the communication, the remote device sends a connection request to the medical device, the connection request containing a session identifier.

15. The method of claim 14, wherein the medical device discards the connection request, if the session identifier is invalid.

16. The method of claim 14, wherein the medical device sends an acknowledgement message to the remote device, if it accepts the connection request, and reads the master key of the session identified by the session identifier of the connection request from storage repository, and wherein the remote device after receipt of the acknowledgement message reads the master key from storage repository, so that cryptographic communication of the application data can commence.

17. A system for establishing cryptographic communications, the system comprising a remote device and a medical device which performs the method of claim 1.

18. A system of claim 17, wherein the medical device is an insulin pump.

* * * * *

UNITED STATES PATENT AND TRADEMARK OFFICE
CERTIFICATE OF CORRECTION

PATENT NO. : 8,472,630 B2  
APPLICATION NO. : 12/939562  
DATED : June 25, 2013  
INVENTOR(S) : Guido Konrad et al.

Page 1 of 1

It is certified that error appears in the above-identified patent and that said Letters Patent is hereby corrected as shown below:

In the Specification:

Col. 1, Line 66, "symmetrickey" should read --symmetric-key--;

Col. 2, Lines 2-3, "are typically s slower" should read --are typically slower--;

Col. 7, Line 22, "SHA™" should read --SHA1--;

Col. 8, Line 2, "trans-port" should read --transport--;

Col. 8, Line 45, "a man-in-the-middle-attack" should read --a man-in-the-middle attack--;

Col. 10, Line 42, "as parameter" should read --as a parameter--;

In the Claims:

Col. 11, Claim 1, Line 12, "; and" should read --;--; and

Col. 12, Claim 13, Line 24, "values the" should read --values, the--.

Signed and Sealed this  
Eighteenth Day of February, 2014

Michelle K. Lee  
*Deputy Director of the United States Patent and Trademark Office*